United States Patent
Xie et al.

(10) Patent No.: US 7,199,370 B2
(45) Date of Patent: Apr. 3, 2007

(54) DEVICE AND METHOD FOR DIGITIZING GAMMA RAY ENERGY AND CHARACTERIZING PEAK TIME AND DECAY TIME CONSTANT WITHOUT THE USE OF ADC

(75) Inventors: Qingguo Xie, Wuhan (CN); Chien-Min Kao, Chicago, IL (US); Zekai Hsiau, Taipei (TW); Chin-Tu Chen, Chicago, IL (US)

(73) Assignee: National Health Research Institutes, Miaoli County (TW)

( * ) Notice: Subject to any disclaimer, the term of this patent is extended or adjusted under 35 U.S.C. 154(b) by 107 days.

(21) Appl. No.: 11/097,121

(22) Filed: Apr. 4, 2005

(65) Prior Publication Data

US 2005/0247879 A1   Nov. 10, 2005

Related U.S. Application Data

(60) Provisional application No. 60/558,709, filed on Apr. 2, 2004.

(51) Int. Cl.
*G01T 1/164* (2006.01)

(52) U.S. Cl. .................... 250/363.03; 250/369

(58) Field of Classification Search .............. 702/79; 250/363.03, 369
See application file for complete search history.

(56) References Cited

U.S. PATENT DOCUMENTS

| | | | | |
|---|---|---|---|---|
| 3,961,271 | A | * | 6/1976 | Zlydak et al. .................. 327/37 |
| 5,378,893 | A | * | 1/1995 | Murray et al. .......... 250/363.03 |
| 6,281,831 | B1 | * | 8/2001 | Shou et al. ................... 341/159 |
| 6,548,997 | B1 | * | 4/2003 | Bronfer et al. ........... 324/76.48 |
| 6,901,337 | B2 | * | 5/2005 | Tanaka et al. ................. 702/60 |
| 7,045,802 | B2 | * | 5/2006 | Vernon ........................ 250/526 |

* cited by examiner

*Primary Examiner*—Constantine Hannaher
(74) *Attorney, Agent, or Firm*—Finnegan, Henderson, Farabow, Garrett & Dunner, L.L.P.

(57) ABSTRACT

A device and method used in high resolution positron emission tomography (PET) systems for digitizing gamma ray energy and characterizing peak time and decay time constant, models a voltage pulse generated upon a PET event detection as a fast linearly rising edge followed by a slower exponential decay. The model includes parameters of the voltage pulse that are relevant for PET event detection including a decay constant, a peak voltage value, and a peak time, which are determined from time interval measurements of the voltage pulse. The time interval measurements are made using comparators and counters in an exemplary electronic implementation.

18 Claims, 13 Drawing Sheets

DEVICE AND METHOD FOR DIGITIZING GAMMA RAY ENERGY AND CHARACTERIZING PEAK TIME AND DECAY TIME CONSTANT WITHOUT THE USE OF ADC

CROSS-REFERENCE TO RELATED APPLICATIONS

This application is based upon and claims the benefit of priority from prior Provisional Application No. 60/558,709, filed on Apr. 2, 2004, the entire contents of which are incorporated herein by reference.

TECHNICAL FIELD

This invention relates to the field of positron emission tomography (PET). More particularly, the present invention relates to signal processing devices and methods used in PET front-end electronics.

BACKGROUND

Positron emission tomography (PET) is a technique used in clinical medicine and biomedical research to create images that show anatomical structures as well as how certain tissues are performing their physiological functions. Radioactive nuclei are introduced into the body as labels on tracer molecules. These nuclei emit positrons which may collide with electrons in the tissue. Each such collision is an annihilation event which may result in two gamma photons. By detecting the gamma photons and processing the result with image processing tools, an image of the activity in the tissue can be produced to display the physiological functions.

In modern PET systems, a scintillation light pulse generated upon the interaction of a photon resulted from; annihilation with a scintillator is collected by photomultiplier tubes (PMT), or avalanche photodiodes (APD), and converted into a charge pulse. Hamamatsu Photonics K.K. Electron Tube Center, *Fundamental and Applications of Photomultiplier Tube*, J P: Hamamatsu Photonics K.K, 1995, the contents of which are hereby incorporated by reference, provides further details on the PMT. The charge pulse is often amplified and filtered to form a new voltage pulse that has a peak amplitude proportional to the area under the original scintillation light pulse, and hence proportional to the amount of photon energy that is deposited in the scintillator during the interaction. The peak amplitude is then sampled and converted into digital data by use of analog-to-digital converters (ADCs) for subsequent processing. An event time is typically obtained by using constant fraction discriminators (CFDs).

In order to achieve high spatial resolution and a large imaging volume, more and more small scintillators are employed in PET design. Since every scintillator output needs to be separately processed, the number of ADC channels in a modern PET system is rapidly increasing. In addition, as faster scintillators and a 3D imaging mode are more widely used, high-speed ADCs are often desirable. However, a PET system that employs a large number of high-speed ADCs not only consumes a large amount of power, but also is often too expensive for many applications.

SUMMARY

Consistent with the present invention, methods and devices may be provided for digitizing gamma ray energy produced in a PET system and characterizing a peak time and a decay time constant without the use of ADCs.

Consistent with the present invention, a method for use in a PET system is performed by digitizing gamma ray energy. The method may include defining a model for a voltage pulse generated by a PET detector; determining a decay time constant, a peak amplitude, and a peak time, as parameters of the voltage pulse model, that are relevant for PET event detection; and computing the determined parameters for the generated voltage pulse.

Also consistent with the present invention, a method for use in a PET system is performed for digitizing gamma ray energy. The method may include defining a voltage pulse generated by a PET detector as a fast linearly rising edge followed by a slower exponential decay and characterized by a decay time constant, a peak amplitude, and a peak time; measuring a plurality of time intervals derived from a received voltage pulse generated by the PET detector based on a plurality of reference voltages; calculating at least the decay time constant, the peak amplitude, and the peak time of the received voltage pulse by using a plurality of time intervals; and outputting results of the calculating in digital format.

Also consistent with the invention, a device for use in PET for digitizing gamma ray energy includes a plurality of comparators, each coupled to receive a PET voltage pulse on a first input, and a first reference voltage on a second input; a plurality of counters, each having at least an enable input, a start input, a stop line, and an output; and a plurality of inverters coupled between outputs of said comparators and start or stop inputs of ones of said counters, the outputs of ones of said comparators coupled to the start or enable inputs of ones of said counters such that said plurality of counters are enabled only during an enable period when an output voltage of one of said comparators that is coupled to receive a lowest reference voltage is positive, and during the enabled period each of said counters starts counting upon a first occurrence of a rising edge of the voltage pulse at its start input and continues counting until a last occurrence of a rising edge at its stop input, and the respective outputs of said counters are digitized time intervals used to determine parameters of the PET voltage pulse for event detection.

Further consistent with the present invention, there is provided a PET system that incorporates the device mentioned above to perform PET.

Also consistent with the present invention, a PET system that uses the method mentioned above may be provided to perform PET.

Also consistent with the present invention, a counter for use in a PET system may be provided to digitize time intervals between a rising edge of a voltage pulse, generated by a PET detector, reaching a reference voltage and the falling edge reaching the reference voltage. The counter may include at least a start input and a stop input, a first register to store a system clock time of a first occurrence of a rising edge received at the start input and to remain unchanged during the entire enabled period; and a second register to store the system clock time when a rising edge occurs at the stop input during the enabled period such that an output of the counter equals a difference between the system clock times stored in the first and second registers.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several aspects of the invention and together with the description, serve to explain the principle of the invention. In the drawings.

DETAILED DESCRIPTION

Reference will now be made in detail to exemplary aspects of the invention, examples of which are illustrated in the accompanying drawings. Wherever possible, the same reference numbers will be used throughout the drawings to refer to the same or like parts.

Figure 1:
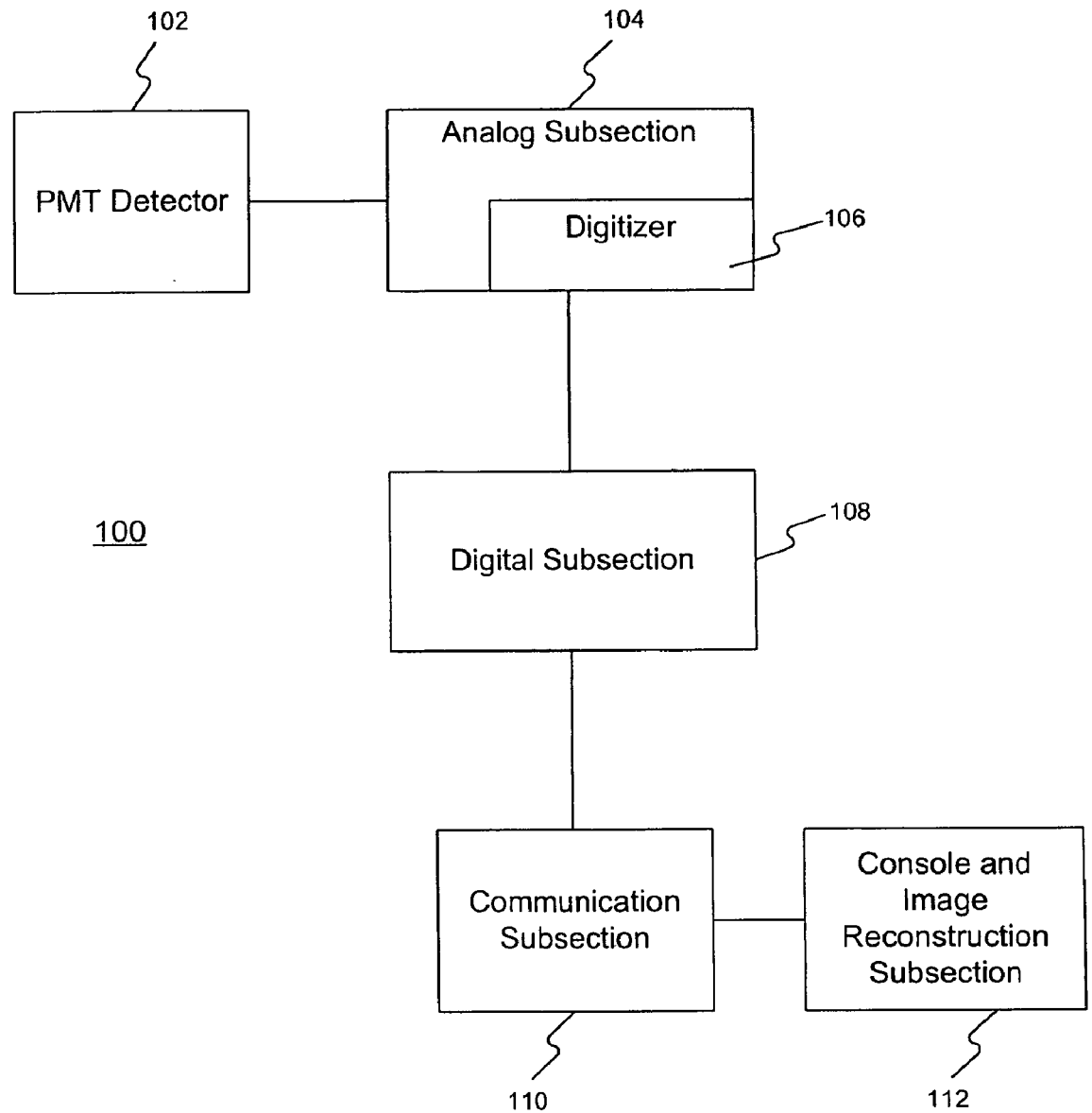
FIG. 1 is a block diagram of an exemplary PET system consistent with the present invention.

FIG. 1 illustrates an exemplary PET system 100 consistent with the present invention. PET system 100 includes a PMT detector 102 to detect light pulses from a scintillator (not shown) and convert the detection result into a charge pulse. Detector 102 includes circuitry for amplifying and filtering the charge pulse to provide a voltage pulse. An analog subsection 104 of PET system 100 receives and processes the voltage pulse. Analog subsection 104 includes a digitizer 106 to digitize the voltage pulse and to provide in digital form to digital subsection 108 parameters of the voltage pulse that are relevant to PET event detection. Digital subsection 108 may perform all of the digital signal processing procedures needed by PET system 100.

The results of the digital processing by digital subsection 108 can be further transmitted to other systems by a communication subsection 110, or displayed on a console and image reconstruction subsection 112. Communication subsection 110 may be any appropriate type of communication system or device used to transmit the results of the digital processing. Console and image reconstruction subsection 112 may include any appropriate type of console device or computer system used to display the results of the digital processing from Digital subsection 108.

Figure 2:
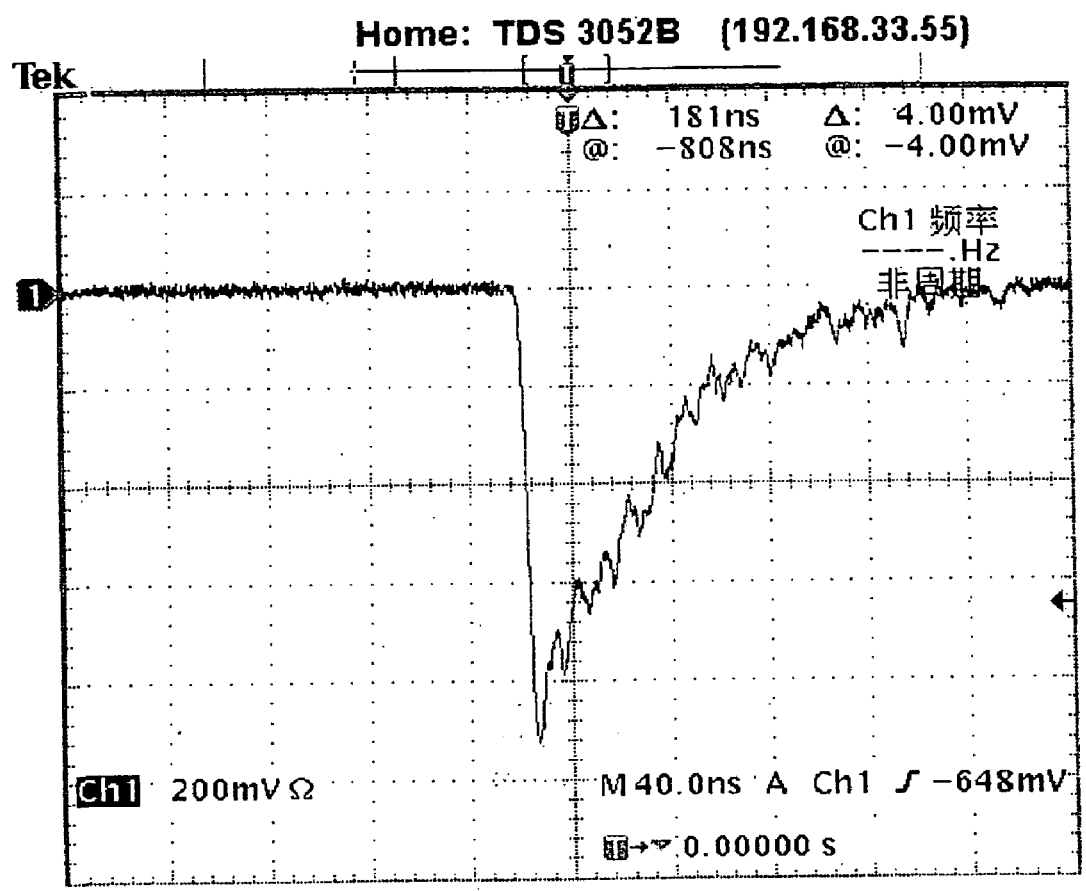
FIG. 2 is a diagram of an example voltage pulse generated by an LSO/PMT detector.

FIG. 2 shows an exemplary voltage pulse generated by a PET detector 102, in particular, a lutetium oxyorthosilicate crystal coupled PMT (LSO/PMT) detector, upon interaction of a gamma ray photon with the LSO. The pulse is measured across a resistor that is directly connected to the LSO/PMT detector. The illustrated exemplary voltage pulse was sampled by using a digital oscilloscope at 5 GHz sampling rate. The peak time and decay constant observed from numerous such pulses are about 10 ns and 40–45 ns, respectively.

Figure 3:
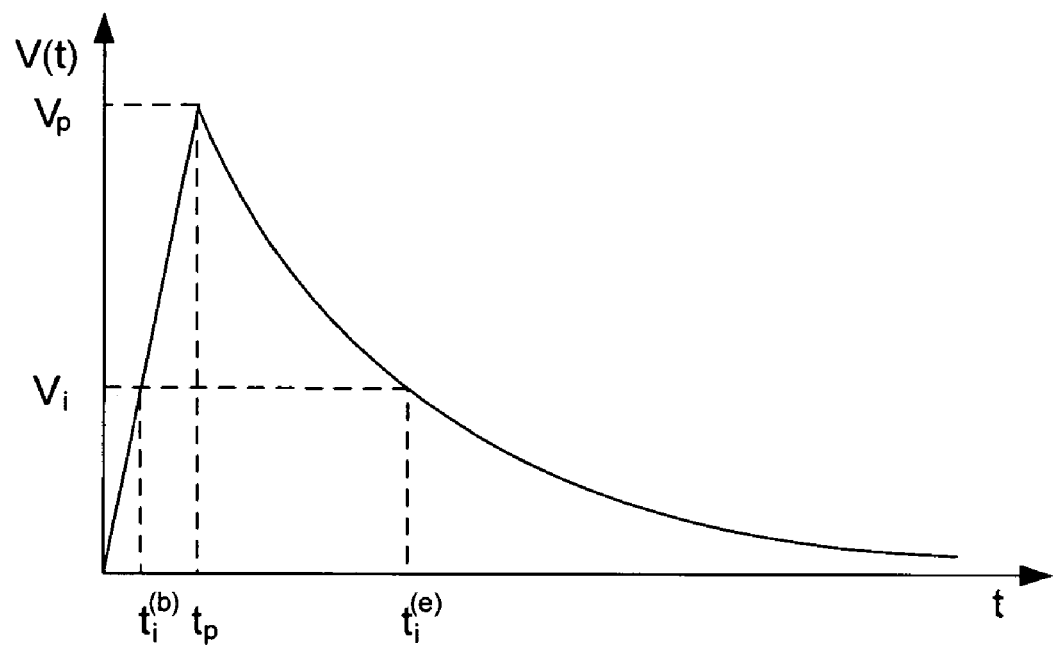
FIG. 3 is a diagram of a functional description of a voltage pulse generated by scintillator/PMT detectors.

FIG. 3 illustrates a general functional description of the voltage pulse. As shown in FIG. 3, when noise is ignored, the voltage pulse can be approximated by a fast, linearly rising edge followed by a slower exponential decay. Therefore, a voltage pulse generated by PMT detector 102, either detected across a resistor or at the output of a modest-gain preamplifier connected to detector 102 can be mathematically modeled as:

$$V(t) = \begin{cases} 0 & t < 0, \\ V_p(t/tp) & 0 < t < tp, \\ V_p e^{-(t-tp)/\tau} & t \geq tp, \end{cases} \quad (1)$$

where $\tau$ is the decay time constant characteristic of the scintillator of PMT detector 102, $t_p$ is the pulse peak time, and $V_p$ is the peak amplitude of the pulse. Typically, $t_p \ll \tau$.

The model may then be used to derive three pulse parameters providing information needed in PET event detection, namely, the peak amplitude $V_p$ of the pulse, the decay time constant $\tau$, and the peak time $t_p$. As a non-limiting example, reasons why the peak amplitude of the pulse $V_p$, the decay time constant $\tau$, and the peak time $t_p$ can be used to represent the voltage pulse are explained next. The peak amplitude $V_p$ is proportional to the area under $V(t)$, and hence to the energy deposited in the scintillator. The decay time constant $\tau$ can provide information for identifying the scintillator that is involved in a particular detection event, when more than one scintillator is used in a PET system. The peak time $t_p$ may be utilized to provide the event time, i.e., the timing information of a detected event that is independent of the pulse amplitude. The event time for the purpose of coincidence detection is conventionally achieved by use of constant fraction discriminators (CFDs).

Based on this pulse model, these three pulse parameters may be readily calculated from a few time intervals derived from the pulse $V(t)$. In addition, these time intervals can be measured by use of relatively inexpensive comparators and counters.

Figure 4:
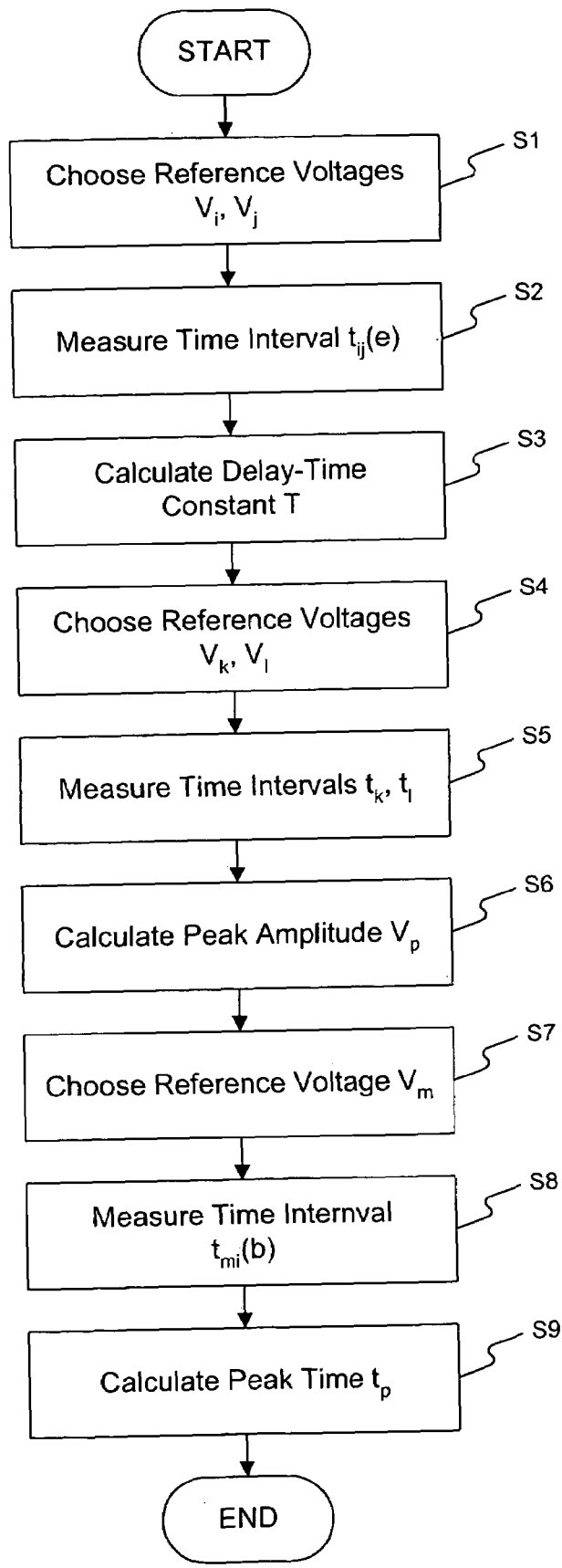
FIG. 4 is a flow chart diagram of an exemplary process to derive the basic properties of a voltage pulse by using a model.

FIG. 4 is a flowchart illustrating steps for deriving the three parameters of the voltage pulse. In step S1, a reference voltage level $V_i$ is chosen such that $V_i < V_p$, and that the model equation $V(t) = V_i$ has two solutions, given by:

$$t_i^{(b)} = t_p(V_i/V_p), \quad (2)$$

$$t_i^{(e)} = t_p - \tau \ln(V_i/V_p), \quad (3)$$

where $t_i^{(b)}$ is the time when $V(t)$ rises above $V_i$ and $t_i^{(e)}$ is the time when $V(t)$ falls below $V_i$. A reference voltage level $V_j$ is chosen such that $V_j < V_i < V_p$, so that $t_j^{(e)} > t_i^{(e)}$, and a time interval $t_{ij}^{(e)} = t_j^{(e)} - t_i^{(e)} = \tau \ln(V_i/V_j) > 0$. In step S2, time interval $t_{ij}^{(e)}$ is measured. In step S3, the decay time constant τ may be calculated as:

$$\tau = t_{ij}^{(e)} / ln(V_i/V_j). \quad (4)$$

In step S4, two other reference voltage levels $V_k$ and $V_l$ are chosen such that $V_k < V_p$, and $V_l < V_p$. Time intervals $t_k = t_k^{(e)} - t_k^{(b)}$, and $t_l = t_l^{(e)} - t_l^{(b)}$ are also defined. Time $t_k^{(b)}$ is the time when V(t) rises above $V_k$ and time $t_k^{(e)}$ is the time when V(t) falls below $V_k$. Time $t_l^{(b)}$ is the time when V(t) rises above $V_l$ and time $t_l^{(e)}$ is the time when V(t) falls below $V_l$. In step S5, the two time intervals $t_k$ and $t_l$ are measured. In step S6, the peak amplitude $V_p$ is calculated.

The following equations can be derived from equations (2) and (3):

$$t_k + \tau ln V_i = (t_p + \tau ln V_p) - V_k(t_p/V_p), \quad (5)$$

$$t_l + \tau ln V_l = (t_p + \tau ln V_p) - V_l(t_p/V_p). \quad (6)$$

Next, equation (6) is subtracted from equation (5) multiplied by $(V_l/V_k)$ to provide:

$$(s+1)t_k - t_l = s(t_p + \tau ln(V_p/V_k)) + \tau ln(s+1), \quad (7)$$

where $s = V_l/V_k - 1$. If $t_p$ is negligible in equation (7), then $$V_p \approx \frac{V_k}{\sqrt[s]{s+1}} \exp\left\{\frac{(s+1)t_k - t_l}{s\tau}\right\}, \quad (8)$$

Since the time constant τ was calculated in step S3, this approximation is valid only when $t_p << \tau ln(V_p/V_k) = \tau ln((s+1) V_p/V_l)$, i.e., under the condition of $$s \gg \frac{V_l}{V_p} \exp\left\{\frac{t_p}{\tau}\right\} - 1. \quad (9)$$

Since voltage $V_l$ is defined to be $V_l < V_p$, and $t_p << \tau$ for many scintillators, the condition shown in equation (9) can be satisfied by using a small s. For example, for $t_p = 10$ ns and τ=40 ns, $V_l$ becomes $1.3(V_l/V_p) - 1$. If $V_l$ is defined as 300 keV corresponding to a $V_p$ of 350 keV, any small s>>0.1 would satisfy the condition above. The condition becomes even more relaxed for scintillators having smaller values of $t_p/\tau$. For example, an s of approximately 1 may be used in certain situations. Other values, however, may also be used without departing the principle of the present invention.

In step S7, another reference voltage $V_m$ is defined such that $V_m < V_p$. A time $t_m^{(b)}$ is defined as the time when V(t) rises above $V_m$. In step S8, a time interval $t_{mi}^{(b)} = t_i^{(b)} - t_m^{(b)}$ is measured. Finally, in step S9, since $V_i = V_p(t_i^{(b)}/t_p)$ and $V_m = V_p(t_m^{(b)}/t_p)$, the peak time $t_p$ is calculated as $$t_p = (V_p/(V_i - V_m))t_{mi}^{(b)}, \quad (10)$$

By using time intervals to derive the three parameters of the voltage pulse, no ADCs and CFDs are needed. Furthermore, when computation speed is of concern, it suffices to obtain only $t_{ij}^{(e)}$, $((s+1)t_k-t_l)/t_{ij}^{(e)}$, and $t_{mi}^{(b)}$. These values may then be used to obtain estimates of τ, $V_p$ and $t_p$ via lookup tables (LUTs).

As another non-limiting example, the calculations may be performed in simpler forms when the reference voltages satisfy $V_l/V_k = V_i/V_j = 2$, and $V_m = V_i/4$. Under these conditions, $s = V_l/V_k - 1 = 1$ and the calculations in steps S3, S6, and S9 are of forms:

$$\tau = t_{ij}^{(e)}/ln2, \quad (11)$$

$$V_p \approx \frac{V_k}{2} \exp\left\{\frac{(2t_k - t_l)ln2}{t_{ij}^{(e)}}\right\}, \quad (12)$$

$$t_p = \frac{2}{3} \frac{V_k}{V_i} \exp\left\{\frac{(2t_k - t_l)ln2}{t_{ij}^{(e)}}\right\} t_{mi}^{(b)}. \quad (13)$$

Although only three parameters of the voltage pulse, five reference voltage levels, and nine detection steps are described with respect to the method shown in FIG. 4, it should be understood that the parameters of the voltage pulse, the reference voltage levels, and detection steps are exemplary and not intended to be limiting. As shown above, assumptions can be applied to reduce the number of reference voltages. Alternatively, other parameters and reference voltages may be added, other detection steps may be added, or the order of the steps may be changed without departing from the principle and scope of the present invention.

Figure 5:
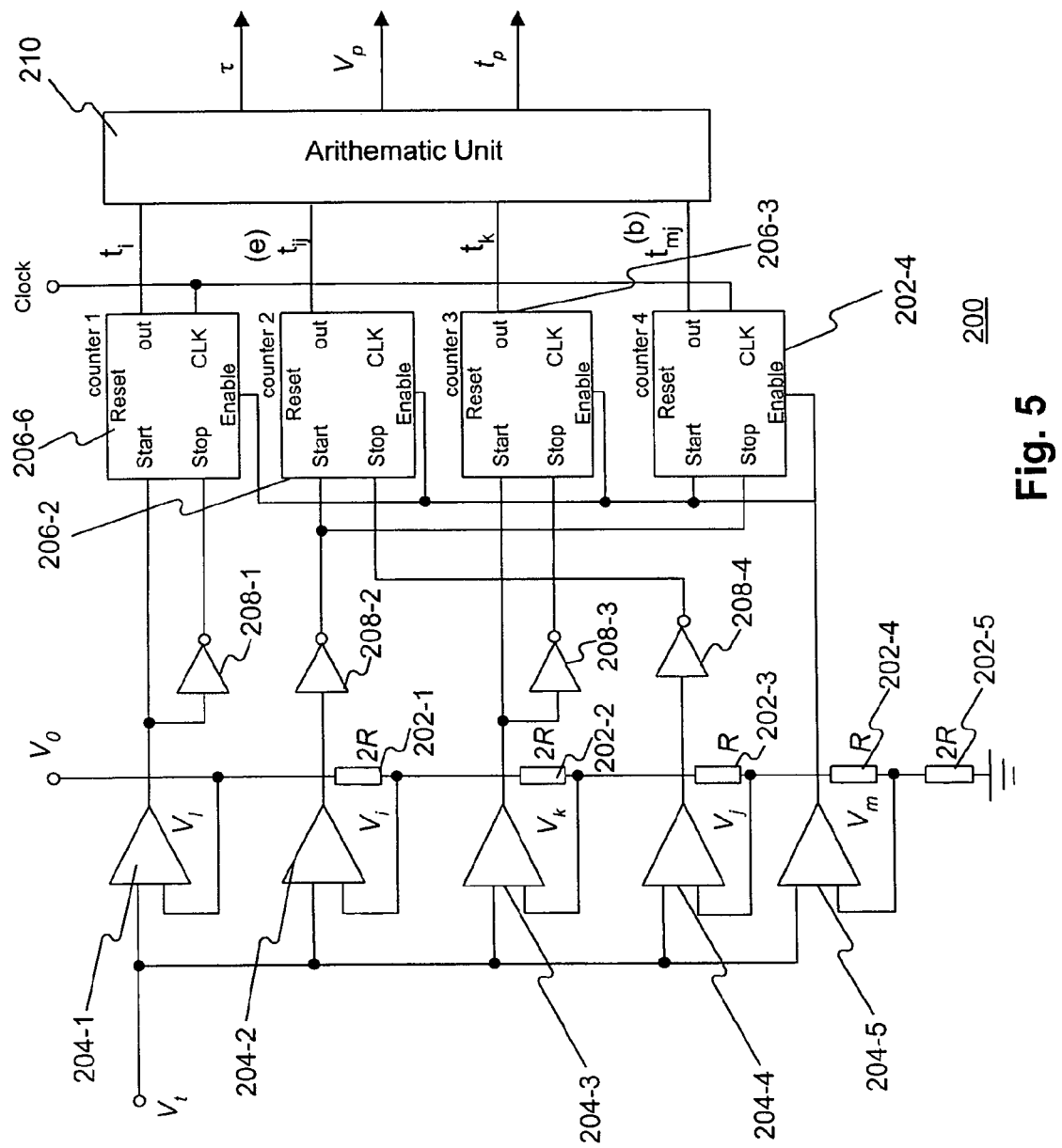
FIG. 5 is a block diagram of an exemplary electronic implementation consistent with the present invention.

FIG. 5 illustrates a conceptual electronic implementation of a digitizer 200 corresponding to digitizer 106 in FIG. 1. The implementation may be based on any appropriate type of mechanisms, such as application specific integrated circuit (ASIC), field programmable gate array (FPGA), and/or a combination of software programs and a microprocessor. As shown in FIG. 5, digitizer 200 comprises a plurality of resistors 202-1 to 202-5, a plurality of comparators 204-1 to 204-5, a plurality of counters 206-1 to 206-4, a plurality of inverters 208-1 to 208-4, and an arithmetic unit 210. Each of counters 206-1 to 206-4 includes "start," "stop," "enable," and "CLK" inputs and an "out" output. The outputs of inverters 208-1, 208-2, 208-3, and 208-4 are coupled to the "stop" inputs of counters 206-1, 206-4, 206-3, and 206-2, respectively. The outputs of comparators 204-1 to 204-4 are coupled to the inputs of inverters 208-1 to 208-4, respectively. The outputs of comparators 204-1 and 204-3 are coupled to the "start" inputs of counters 206-1 and 206-3, respectively. The output of inverter 208-2 is coupled to the "start" input of counter 206-2. The output of comparator 204-5 is coupled to the "start" input of counter 206-4 and the "enable" inputs of counters 206-1 to 2064. The respective "CLK" clock inputs of counters 206-1 to 206-4 are coupled to receive a system clock input.

A first input of each comparator 204-1 to 204-5 is coupled to receive the voltage pulse V(t). Resistors 202-1 to 202-5 are coupled in series between an input for receiving the reference voltage $V_0$ and ground. In one implementation, the resistance values of resistors 202-1 and 202-2 are twice the values of resistors 202-3, 202-4, and 202-5. A second input of comparator 204-1 is coupled to receive reference voltage $V_0$. The second inputs of comparators 204-2 to 204-5 are coupled to receive reference voltage $V_0$ through one or more of resistors 202-1 to 202-5 as shown in FIG. 5. The respective outputs of counter 206-1 to 206-4 are $t_i$, $t_{ij}^{(e)}$, $t_k$, and $t_{mi}^{(b)}$, all of which were previously defined. These outputs are applied to arithmetic unit 210 which performs the computation described above to determine the three voltage pulse parameters, i.e., the decay time constant τ, the peak voltage amplitude $V_p$, and the peak time $t_p$, in digital form.

The inputted voltage pulse V(t) may or may not be pre-amplified. The inputted reference voltage $V_0$ determines the lowest photon energy that can be determined. From the voltage $V_0$, the five reference voltages may be generated by using a simple resistive voltage divider formed by the series connection of resistors 202-1 to 202-5. As a result, comparators 204-1 to 204-5 receive on their second inputs $V_i$, $V_l$, $V_k$, $V_j$, and $V_m$, respectively. For achieving more flexible selections of the reference voltages, programmable resistors may also be employed.

Resistors 202-1 to 202-5 may be any resistors, variable or non-variable, programmable or non-programmable. Resistors 202-1 to 202-5 may be selected so that the five reference voltages described with reference to FIG. 4 satisfy $V_i/V_k=V_l/V_j=2$, and $V_m=V_i/4$.

During the operation of digitizer 200, the rising edge of the output signal of comparator 204-5 signals the occurrence of a detection event. In addition, all of counters 206-1 to 206-4 are enabled only during the period when the output of comparator 204-5 is positive, i.e., when the input voltage V(t) is above $V_m$. Each of counters 206-1 to 2064 is coupled to operate so that during an enabled period, the counter starts counting upon the first occurrence of a rising edge at its "start" input and continues counting until the last occurrence of a rising edge at its "stop" input. After an event is completed, counters 206-1 to 206-4 are reset to zero by the falling edge of a logic pulse and are then ready to handle the next event. Although each of counters 206-1 to 206-4 is illustrated with a "reset" input, the reset logic is not shown. The reset logic may include any appropriate type of reset logic. Generation of the resetting logic pulse is triggered by the rising edge of the output of comparator 204-5. For example, for LSO scintillators, a pulse duration of about 100 ns should be adequate.

Each of counters 206-1 to 206-4 may be implemented by use of two registers. One of the two registers stores the system clock time of the first occurrence of a rising edge at the counter "start" input and remains unchanged during the entire enabled period. The second register stores the system clock time whenever a rising edge occurs at the counter "stop" input during the enabled period. The counter output then equals the difference between the contents of the two registers. For a noiseless voltage pulse, exactly one rising and one falling edge will be produced at the output of each of comparators 204-1 to 204-5 during an enabled period. Therefore, the content of each counter 206-1 to 206-4 provides discrete approximations to the time intervals $t_{ij}^{(e)}$, $t_l$, $t_k$, and $t_{mi}^{(b)}$, respectively. For a noisy voltage pulse, however, multiple rising and falling edges can be produced during one enabled period at the output of one or more of comparators 204-1 to 204-5 and the counters may avoid generating time interval measurements that are much shorter than the actual durations of the intervals. For example, appropriate types of hysteresis comparators may be used for such purposes.

Arithmetic unit 210 calculates the decay time constant τ, the peak amplitude $V_p$, and the peak time $t_p$ from the time intervals $t_{ij}^{(e)}$, $t_l$, $t_k$, and $t_{mi}^{(b)}$ outputted by counters 206-1 to 206-4, respectively, by using the method described in FIG. 4. The calculation may be done by using the above described equations or by lookup tables to speed up the calculation process.

For fast scintillators such as LSO, the values of $t_j$, $t_l$, $t_k$, and $t_i$ are expected to be in the range of 40–100 ns. Therefore, a 1 GHz clock rate may be sufficient for generating accurate estimates of the required time intervals. The voltage $V_0$ can be determined during calibration. For example, after obtaining $V_p$ corresponding to 511 keV with a calibration source (e.g., Ge-68) and a sufficiently small initial $V_0$, a new $V_0$ corresponding to for example, 300 keV can then readily be calculated.

The remaining FIGS. 6A–9 illustrate results of computer-simulation studies conducted to evaluate the performance of an embodiment consistent with the present invention. The computer simulation is performed based on the above described equations. The performance may be affected by at least three factors: (1) error in the pulse model (modeling error); (2) noise in the pulse; and (3) the finite clock rate. Modeling error may cause incorrect estimates of the derived pulse parameters; noise may result in random error in generated time intervals; and the finite clock rate may introduce quantization error of measured time intervals, even when noise is absent. Computer-simulation studies are conducted to examine the effects of the noise and the finite clock rate factors.

Only shot noise is considered when obtaining a noisy output pulse for computer simulation. Shot noise is a major noise component of the charge pulse generated by a scintillator/PMT detector. This noise component arises from the stochastic characteristic of the generation of the scintillation photons and of the electron amplification in PMT. Other sources of noise, such as electronic noise and thermal noise, can be reduced by proper electronic design; they were therefore not included in the simulation studies. Dark current of the PMT was also ignored since it is often not important in pulse detection.

When assuming that the voltage pulse V(t) is obtained by directly coupling the PMT output current to a resistor, the shot noise can be obtained as $$\phi(t)=\gamma N(V(t)/V(t_p))$$

where $\gamma=\eta/((t_p+2\tau)FB)$, N is the total number of scintillation photons generated in one detection event, $\eta$ is the quantum efficiency of the PMT, F is the noise figure of the PMT, and B is the bandwidth of the measurement system.

In the simulation, typical values of $\eta=0.2$ and $F=1.2$ for the PMT were used. For the scintillation light pulses, the total number of photons generated upon the deposition of per 1 MeV energy in LSO and BGO were taken to be $2.7\times10^4$ and $8.2\times10^3$, respectively. The decay time constant and peak time of the voltage pulse depend not only on the type of the scintillator, but also on the bandwidth of the analog portion of the measurement system. The decay time constants of 40 ns and 300 ns for the pulses generated by LSO/PMT and BGO/PMT, respectively, were used. A 10 ns peak time was assumed for both detectors. In practice, the bandwidth of the measurement system, B, should be limited by the bandwidth of the comparators and a B=40 MHz is used for two reasons. First, this bandwidth, considered high for comparators, can support the 10 ns rise time, and the longer 40 ns and 300 ns decay times. Second, relatively inexpensive comparators to provide this bandwidth are available. With these settings, the SNR $\phi(t)$ of the resulting voltage pulse was determined with $\gamma \approx 0.05$ for LSO/PMT and $\gamma \approx 0.007$ for BGO/PMT. Once $\phi(t)$ was determined, at a given time t a Gaussian noise having a standard deviation $V(t)/\sqrt{\phi(t)}$ was added to V(t) to obtain a noisy output pulse. Finally, the occurrence times of the generated pulses were made random with respect to the system clock.

Figure 6A:
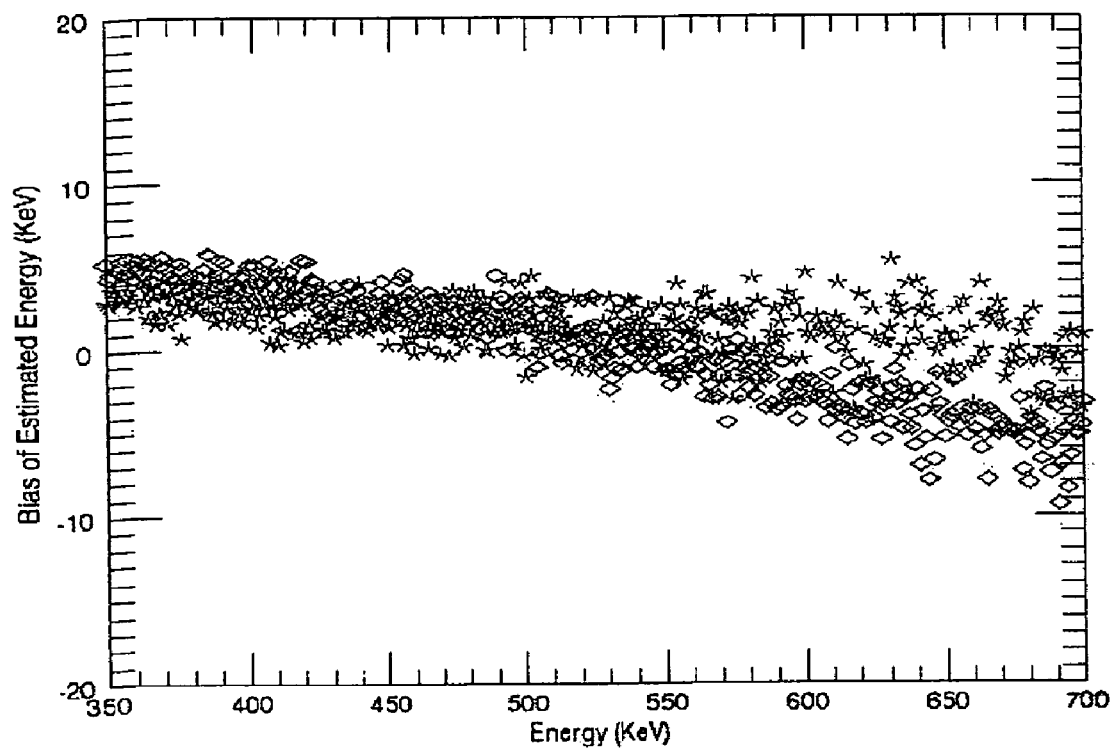
FIGS. 6A, 6B, and 6C are graphical representations of biases of an estimated photon energy, a peak time, and a decay time constant for a lutetium oxyorthosilicate crystal coupled PMT (LSO/PMT) as functions of the photon energy.
Figure 6B:
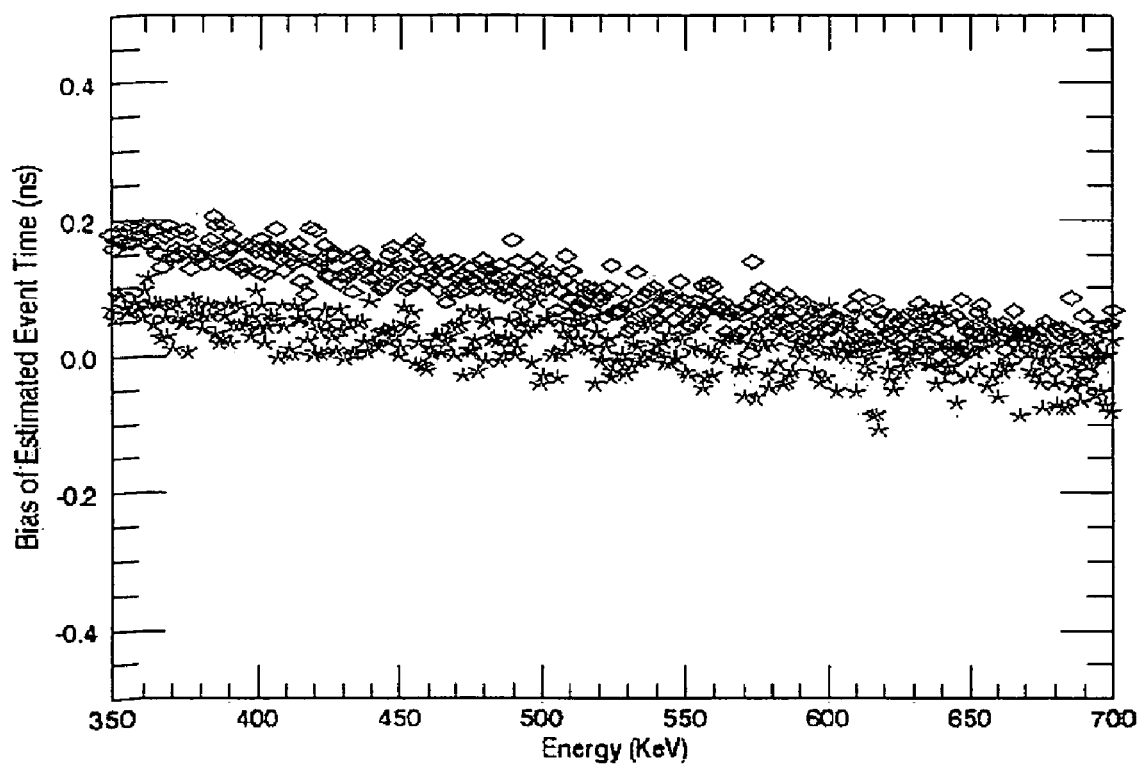
Figure 6C:
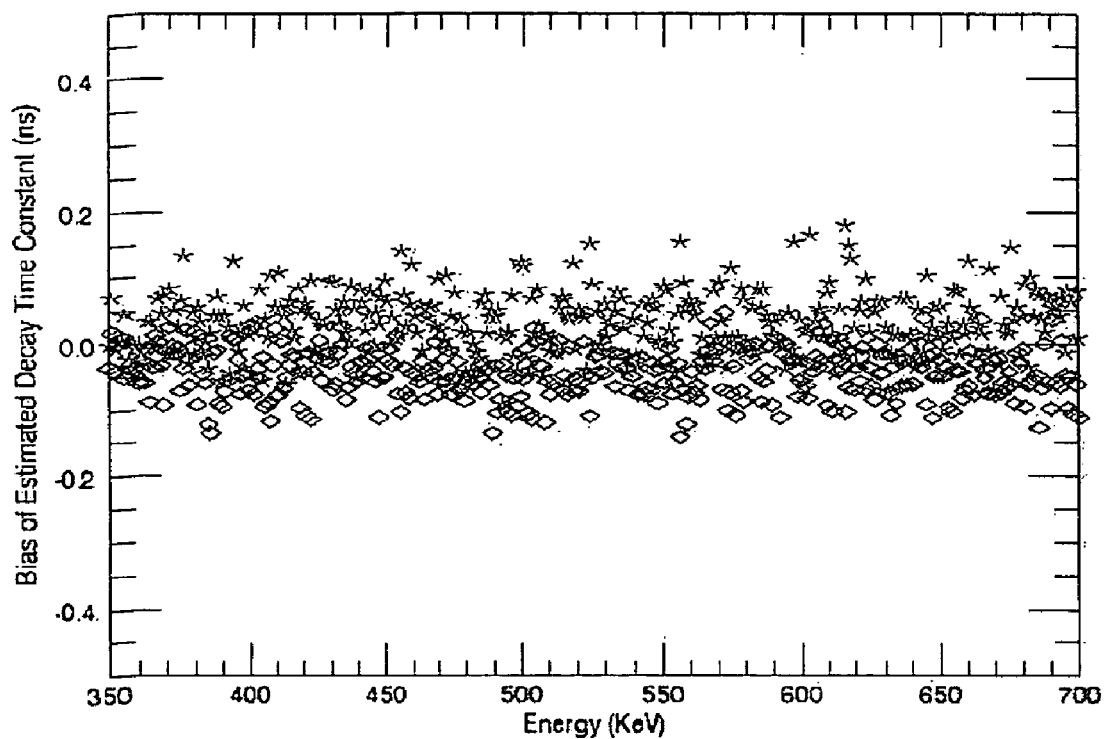

At each photon energy E ranging from 350 keV to 700 keV, 1000 noisy events for LSO/PMT were generated. FIGS. 6A, 6B, and 6C show the biases of the estimated results as functions of the photon energy ranging from 350 keV to 700 keV using two system clock rates of 3.5 GHz and 1 GHz, respectively. FIG. 6A shows a bias of estimated energy for LSO/PMT as a function of the photon energy when the decay time constant τ=40 ns and the peak time $t_p$=10 ns. FIG.

6B shows a bias of estimated peak time $t_p$ for LSO/PMT as a function of the photon energy when the decay time constant T=40 ns and the peak time $t_p$=10 ns. FIG. 6C shows a bias of estimated decay time constant T for LSO/PMT as a function of the photon energy when the decay time constant T=40 ns and the peak time $t_p$=10 ns. In FIGS. 6A–6C, the symbol "*" represents the results obtained by using 3.5 GHz clock rate, and the symbol "◇" represents the results obtained by using 1 GHz clock rate.

Generally speaking, the biases were small and the differences between the results obtained with 3.5 GHz and 1 GHz clock rates were not significant. It is noted that the bias of the estimated photon energy obtained by using the 3.5 GHz clock is slightly larger in magnitude than that obtained by using the 1 GHz clock. In addition, the results are over-estimated at energies below 511 keV, and under-estimated at energies above 511 keV, when the calibration of the photon energy was performed at 511 keV.

Figure 7A:
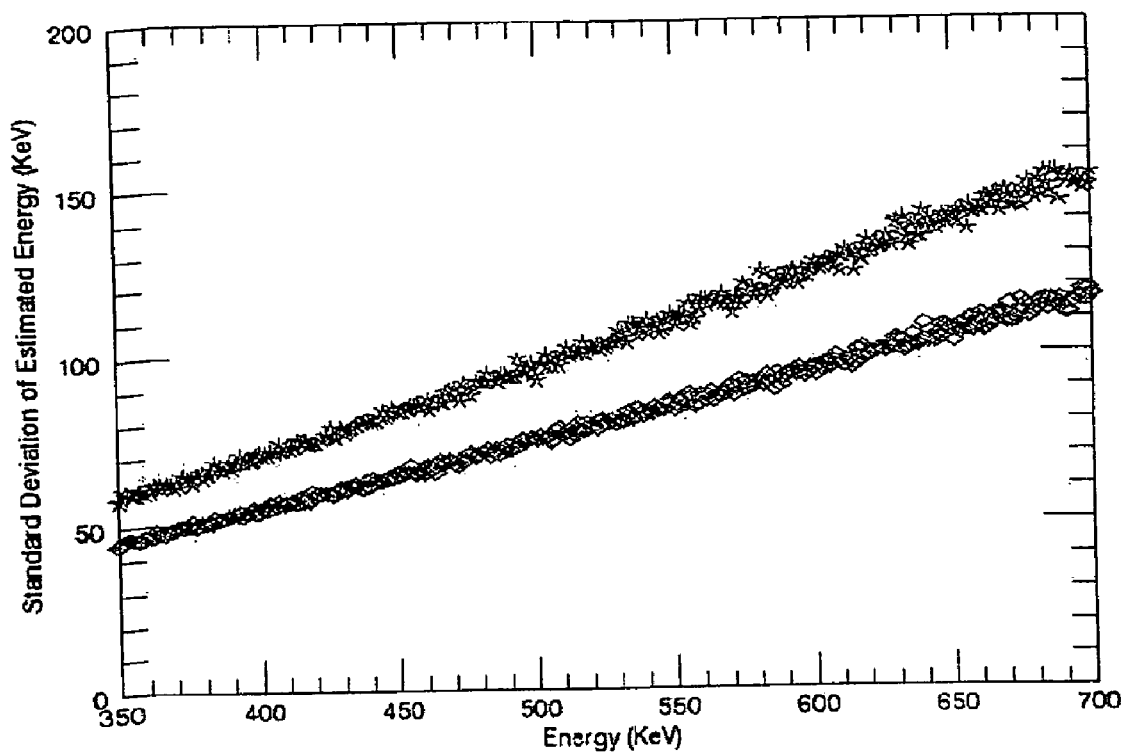
FIGS. 7A, 7B, and 7C are graphical representations of standard deviations of an estimated photon energy, a peak time, and a decay time constant for LSO/PMT as functions of the photon energy.
Figure 7B:
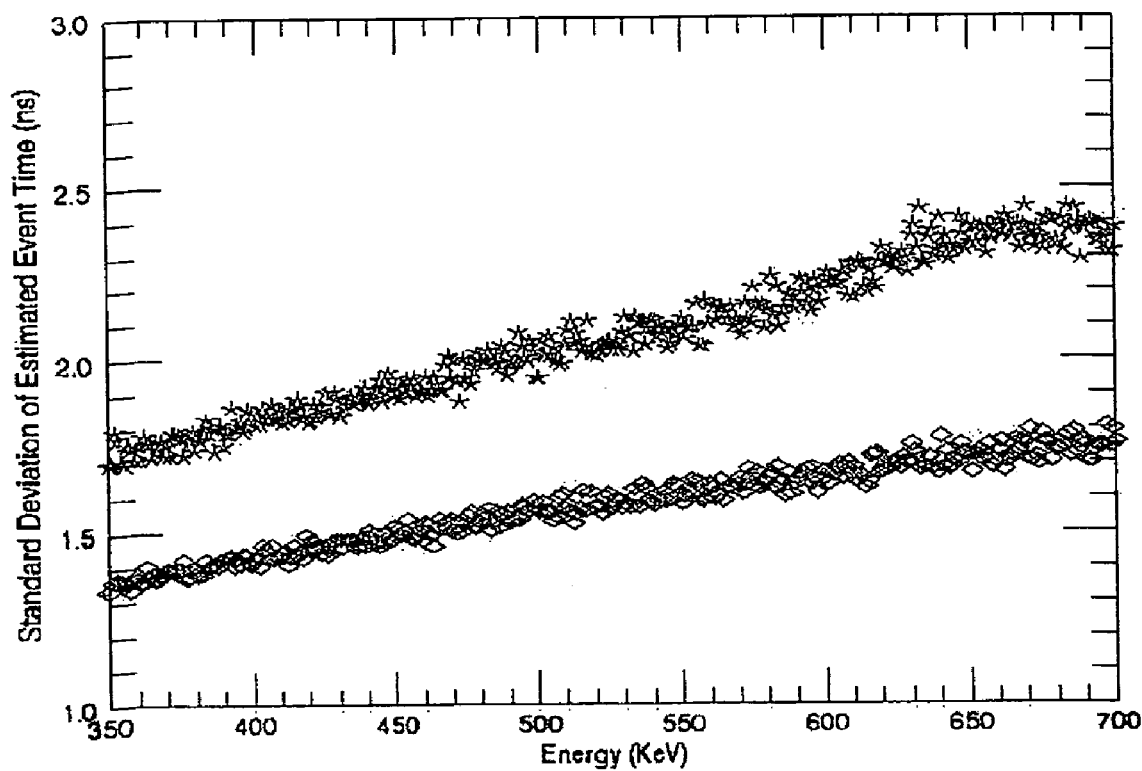
Figure 7C:
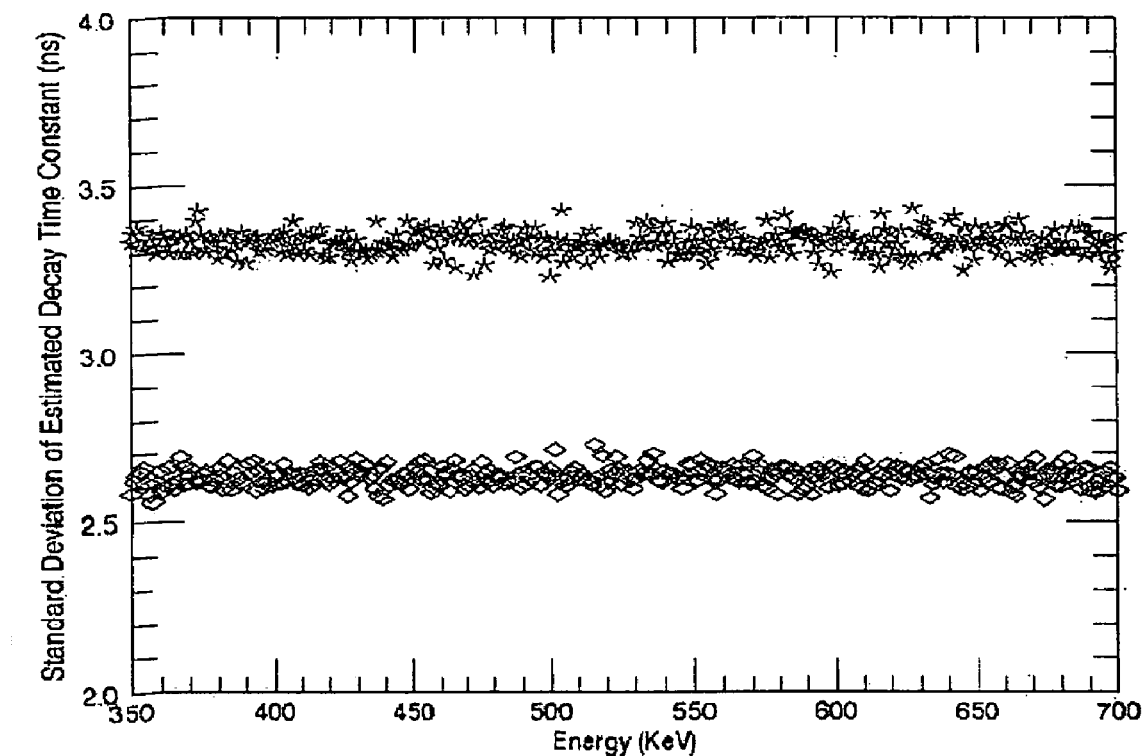

FIGS. 7A, 7B, and 7C show the standard deviations of the estimated results as functions of the photon energy using two system clock rates of 3.5 GHz and 1 GHz, respectively. FIG. 7A shows the standard deviation of estimated energy for LSO/PMT as a function of the photon energy when the decay time constant T=40 ns and the peak time $t_p$=10 ns. FIG. 7B shows the standard deviation of estimated peak time $t_p$ for LSO/PMT as a function of the photon energy when the decay time constant T=40 ns and the peak time $t_p$=10 ns. FIG. 7C shows the standard deviation of estimated decay time constant T for LSO/PMT as a function of the photon energy when the decay time constant T=40 ns and the peak time $t_p$=10 ns. In FIGS. 7A–7C, the symbol "*" represents the results obtained by using 3.5 GHz clock rate, and the symbol "◇" represents the results obtained by using 1 GHz clock rate.

The results shown in FIG. 7A–7C indicated that estimates obtained by using the higher 3.5 GHz clock rate had significantly smaller standard deviations than those obtained by using the lower 1 GHz clock rate. This may be attributed to the randomness of the event occurrence time with respect to the system clock. This randomness introduces random errors in the measured time intervals $t_{ij}^{(e)}$, $t_l$, $t_k$, and $t_{mi}^{(b)}$, and hence in quantities derived from them. On average, the errors were larger when a slower clock is used. Also, the standard deviations of the estimated photon energy and peak time increased approximately linearly with the photon energy, with the 3.5 GHz case showing smaller rates of increase. This is consistent with the fact that noise energy of the voltage pulses increases linearly with the photon energy. In contrast, the standard deviation of the estimated decay time constant shows no observable dependence on the photon energy.

TABLE 1

The biases and FWHMs obtained for LSO/PMT (tp = 10 ns and T = 40 ns) at E = 511 keV when using 3.5 GHz and 1 GHz clocks.

| clock rate | | E | $t_p$ | T |
|---|---|---|---|---|
| 3.5 GHz | bias | 0.65 keV | 0.07 ns | 0.02 ns |
| | FWHM | 154.0 keV | 3.3 ns | 4.5 ns |
| 1 GHz | bias | 3.02 keV | 0.03 ns | 0.04 ns |
| | FWHM | 170.0 keV | 4.2 ns | 7.5 ns |

Table 1 summarizes experimentally determined biases and full-width-at-half-maxima (FWHMs) of the estimated photon energy, event time, and decay time constant obtained at E=511 keV. These results show that the estimated photon energy obtained are in good agreement-with the actual values. The FWHMs observed for the photon energy correspond to energy resolutions of about 30% and 33% at 511 keV when using 3.5 GHz and 1 GHz clock rates, respectively. The FWHMs in the event time indicate that it is possible to employ a coincidence window of 10 ns and 12 ns without significantly losing true coincidence events, when using 3.5 GHz and 1 GHz clock rates, respectively. Finally, the small FWHMs obtained for the decay time constant may suggest that the scintillator crystal used in the PMT can be effectively identified based on the decay time constants.

TABLE 2

The bias and FWHMs obtained for BGO/PMT (tp = 10 ns and T = 300 ns) at E = 511 keV when using 1 GHz clock.

| SNR | | E | $t_p$ | T |
|---|---|---|---|---|
| x1 | bias | 1482 keV | 47.7 ns | 0.10 ns |
| | FWHM | 29178 keV | 662.4 ns | 100 ns |
| x10 | bias | 0.96 keV | 0.06 ns | 0.46 ns |
| | FWHM | 180.0 keV | 4.2 ns | 54.0 ns |

Table 2 summarizes the bias and FWHMs of the estimated photon energy, event time, and decay time constant obtained at E=511 keV for BGO/PMT by using the 1 GHz clock. SNR×10 shows the results obtained if the SNR of the generated pulse can be made 10-fold. This higher SNR level may be achieved by employing a PMT of higher quantum efficiency and/or by reducing the bandwidth of the measurement system. With this higher SNR, reasonably good results can be obtained. In addition, BGO/PMT may be more commonly modeled as having 8.5% of light being emitted with a 60 ns decay-time constant and the remaining 91.5% of light being emitted with a 300 ns decay-time constant.

TABLE 3

The bias and FWHMs obtained for BGO/PMT (tp = 10 ns and T = 300 ns) at E = 511 keV when using 1 GHz clock with generated pulses contain a 60 ns decay component and a 300 ns decay component.

| SNR | | E | $t_p$ | T |
|---|---|---|---|---|
| x10 | bias | 0.23 keV | 0.08 ns | 0.02 ns |
| | FWHM | 140.0 keV | 4.2 ns | 48.0 ns |

Table 3 shows the results obtained when applying the method consistent with the present invention to pulses generated with dual-exponential decay components modeled as having 8.5% of light being emitted with a 60 ns decay time constant and the remaining 91.5% being emitted with a 300 ns decay time constant with the ×10 SNR level. Even though the method consistent with the present invention is derived from the single-exponential model, the results indicate that good estimates can still be obtained when the SNR of the pulse is adequate.

Figure 8:
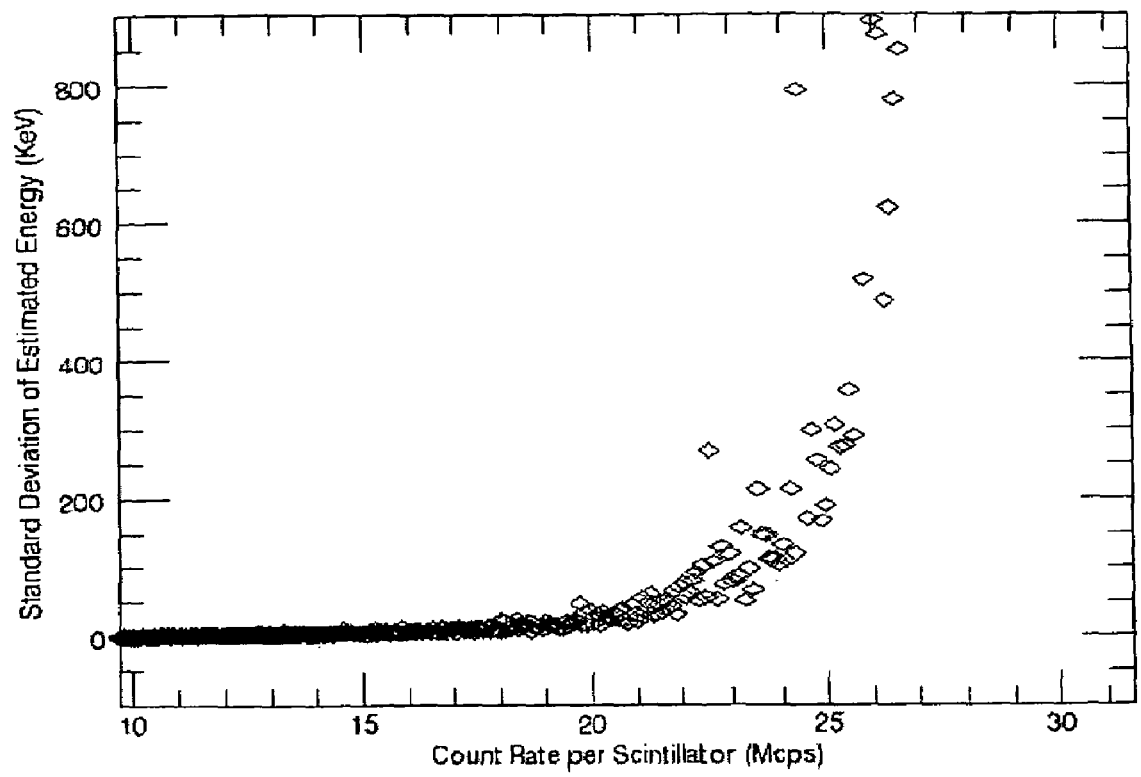
FIG. 8 is a graphical representation of the standard deviations of the estimated photon energy at E=511 keV as a function of an operating event-rate for an LSO/PMT.
Figure 9:
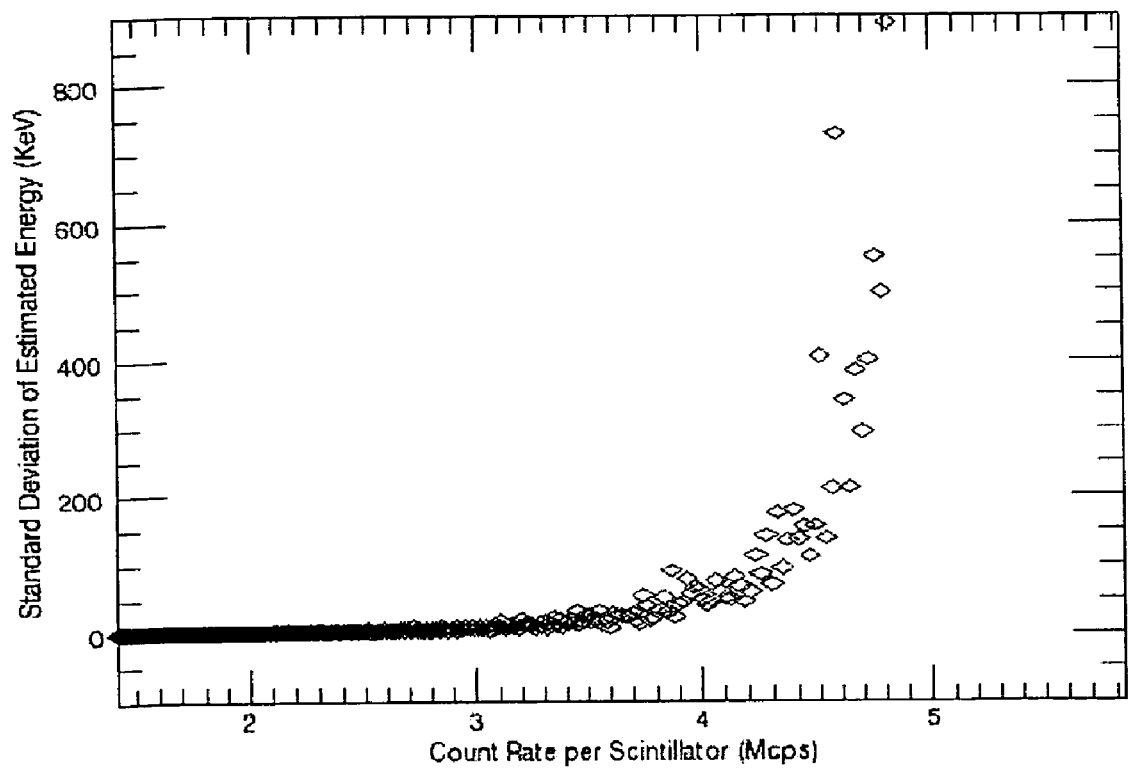
FIG. 9 is a graphical representation of the standard deviations of the estimated photon energy at E=511 keV as a function of the operating event-rate for bismuth germinate crystal coupled PMT (BGO/PMT).

FIG. 8 illustrates the standard deviation of the estimated photon energy at E=511 keV as a function of the-operating event-rate for LSO/PMT using a 3.5 GHz clock. FIG. 9 illustrates the standard deviation of the estimated photon energy at E=511 keV as a function of the operating event-rate for BGO/PMT using a 1 GHz clock with the ×10 SNR level. At high count rates, event pileups can become non-negligible, and lead to incorrect measurements of the time intervals, especially for time intervals derived from the use of small reference voltages. Therefore, in practicing embodiments consistent with the present invention for high count-rate applications, it would be reasonable to use larger reference voltages to mitigate the effects of pileups on the measured time intervals. Increasing the reference voltages, however, will decrease the durations of the time intervals. As a result, the measured time intervals, and hence the resulting estimates, will be more susceptible to noise. FIGS. 8 and 9 show the estimated results suggesting that a 20 million-count-per-second (Mcps) operating count-rate may be achieved for LSO/PMT and 4 Mcps for BGO/PMT.

Other embodiments consistent with the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for use in positron emission tomography (PET) for digitizing gamma ray energy, comprising:
    defining a model for a voltage pulse generated by a PET detector;
    determining a decay time constant, a peak amplitude, and a peak time, as parameters of the voltage pulse model, that are relevant for PET event detection; and
    computing the determined parameters for the generated voltage pulse.

2. The method in claim 1, wherein defining the model further comprises:
    modeling the voltage pulse by a fast linearly rising edge followed by a slower exponential decay.

3. The method in claim 2, wherein the determining further comprises:
    providing a plurality of reference voltages;
    measuring a plurality of time intervals derived from the generated voltage pulse based on the reference voltages; and
    calculating the determined parameters of the generated voltage pulse by using the plurality of time intervals.

4. The method in claim 1, wherein determining further comprises:
    defining the voltage pulse as V(t), the decay time constant as $\tau$, the peak amplitude as $V_p$, and the peak time as $t_p$;
    determining the decay time constant $\tau$ as $t_{ij}^{(e)}/\ln(V_i/V_j)$, wherein $V_i$ and $V_j$ are predetermined reference voltage levels such that $V_j < V_i$ and both $V_j$ and $V_i$ are less than the peak amplitude $V_p$ of the voltage pulse, and $t_{ij}^{(e)}$ is a time interval between a time when the voltage pulse V(t) falls below $V_j$ and a time when the voltage pulse V(t) falls below $V_i$;
    determining the peak amplitude $V_p$ as $$\frac{V_k}{\sqrt[s]{s+1}} \exp\left\{\frac{(s+1)t_k - t_l}{s\tau}\right\},$$

wherein $s = V_l/V_k - 1$, $V_l$ and $V_k$ are predetermined reference voltage levels such that both $V_l$ and $V_k$ are less than $V_p$, $t_l$ is a time interval between a time when the voltage pulse V(t) falls below $V_l$ and a time when the voltage pulse V(t) rises above $V_l$, and $t_k$ is a time interval between a time when the voltage pulse V(t) falls below $V_k$ and a time when the voltage pulse V(t) rises above $V_k$; and
    determining the peak time $t_p$ as $(V_p/(V_i - V_m))t_{mi}^{(b)}$, wherein $V_m$ is a predetermined reference voltage level such that $V_m$ is less than $V_p$, and $t_{mi}^{(b)}$ is a time interval between a time when the voltage pulse V(t) rises above $V_i$ and a time when the voltage pulse V(t) rises above $V_m$.

5. The method in claim 3, further including measuring the plurality of time intervals by using counters.

6. The method in claim 3, wherein the calculating of the determined parameters further comprises:
    deriving the decay time constant using the measured plurality of time intervals.

7. The method in claim 3, wherein the calculating of the determined parameters further comprises:
    determining the peak amplitude of the voltage pulse using the measured plurality of time intervals.

8. The method in claim 3, wherein the calculating of the determined parameters further comprises:
    determining the peak time of the voltage pulse using the measured plurality of time intervals.

9. A method in positron emission tomography (PET) for digitizing gamma ray energy, comprising:
    defining a voltage pulse generated by a PET detector as a fast linearly rising edge followed by a slower exponential decay and characterized by a decay time constant, a peak amplitude, and a peak time;
    measuring a plurality of time intervals derived from a received voltage pulse generated by the PET detector based on a plurality of reference voltages;
    calculating at least the decay time constant, the peak amplitude, and the peak time of the received voltage pulse by using a plurality of time intervals; and
    outputting results of the calculating in digital format.

10. The method in claim 9, further including performing the calculating using an arithmetic unit.

11. The method in claim 9, further including performing the calculating using data stored in a lookup table.

12. A device for use in positron emission tomography (PET) for digitizing gamma ray energy, comprising:
    a plurality of comparators, each coupled to receive a PET voltage pulse on a first input, and a first reference voltage on a second input;
    a plurality of counters, each having at least an enable input, a start input, a stop input, and an output; and
    a plurality of inverters coupled between outputs of said comparators and start or stop inputs of ones of said counters,
    the outputs of ones of said comparators coupled to the start or enable inputs of ones of said counters such that said plurality of counters are enabled only during an enable period when an output voltage of one of said comparators that is coupled to receive a lowest reference voltage is positive, and during the enabled period each of said counters starts counting upon a first occurrence of a rising edge of the voltage pulse at its start input and continues counting until a last occurrence of a rising edge at its stop input, and the respective outputs of said counters are digitized time intervals used to determine parameters of the PET voltage pulse for event detection.

13. The device in claim 12, further comprising:
    at least one arithmetic unit for calculating and outputting the parameters of the voltage pulse using the time intervals outputted by said counters.

14. The device in claim 13, wherein the parameters of the voltage pulse include the decay time constant, the peak amplitude, and the peak time.

15. The device in claim 12, further comprising:
means for providing a set of desirable reference voltages used to calculate the parameters of the voltage pulse.

16. A PET system that incorporates the device in claim 12.

17. A PET system that uses the method in claim 1.

18. A counter, for use in a positron emission tomography (PET) system, having at least a start input and a stop input, for digitizing time intervals between a rising edge of a voltage pulse, generated by a PET detector, reaching a reference voltage and the falling edge reaching the reference voltage, comprising:

a first register to store a system clock time of a first occurrence of a rising edge received at the start input and to remain unchanged during the entire enabled period; and a second register to store the system clock time when a rising edge occurs at the stop input during the enabled period such that an output of the counter equals a difference between the system clock times stored in the first and second registers.

* * * * *